United States Patent [19]
Ward et al.

[11] Patent Number: 5,474,533
[45] Date of Patent: Dec. 12, 1995

[54] INTRATHORACIC MECHANICAL, ELECTRICAL AND TEMPERATURE ADJUNCT TO CARDIOPULMONARY CEREBRAL RESUSCITATION, SHOCK, HEAD INJURY, HYPOTHERMIA AND HYPERTHERMIA

[75] Inventors: Kevin R. Ward; Charles G. Brown; Roger R. Dzwonczyk, all of Columbus, Ohio

[73] Assignee: The Ohio State University, Columbus, Ohio

[21] Appl. No.: 225,835

[22] Filed: Apr. 11, 1994

[51] Int. Cl.⁶ ............................ A61M 39/00; A61M 16/00
[52] U.S. Cl. ................. 604/26; 604/51; 604/101; 604/113; 604/114
[58] Field of Search ........................ 604/26, 20–22, 604/23–25, 27, 28, 45, 48, 51, 96–99, 101–104, 113, 264, 174

[56] References Cited

U.S. PATENT DOCUMENTS

| | | |
|---|---|---|
| 4,198,963 | 4/1980 | Barkalow et al. |
| 4,928,674 | 5/1990 | Halperin et al. |
| 5,002,557 | 3/1991 | Hasson . |
| 5,006,109 | 4/1991 | Douglas et al. |
| 5,098,375 | 3/1992 | Baier . |
| 5,139,478 | 8/1992 | Koninckx et al. |
| 5,176,697 | 1/1993 | Hasson et al. |
| 5,197,491 | 3/1993 | Anderson et al. |
| 5,199,944 | 4/1993 | Cosmescu . |
| 5,226,876 | 7/1993 | Filipi et al. |
| 5,246,419 | 9/1993 | Absten . |
| 5,334,183 | 8/1994 | Wuchinich . |
| 5,362,310 | 11/1994 | Semm . |
| 5,364,372 | 11/1994 | Danks et al. |

FOREIGN PATENT DOCUMENTS

92/06681   4/1992   WIPO .

*Primary Examiner*—C. Fred Rosenbaum
*Assistant Examiner*—Perry E. Van Over
*Attorney, Agent, or Firm*—Frank H. Foster; Kremblas, Foster, Millard & Pollick

[57] ABSTRACT

A method and apparatus for treating patients suffering from one or more of the conditions of cardiac arrest, shock, respiratory failure, hypothermia, hyperthermia and head injury. Chest tubes are inserted through respective holes in each hemithorax of the patient and attached to a gas source and an exhaust pump with connections and valves for alternately inflating and deflating a patient's thoracic cavity with a gas. A gas regulator, including heat exchanger, is interposed between the gas source and the tubes for warming or cooling the gas, and an electrode is mounted on the tubes and connected through a wire to electronic medical equipment. Collapsed seals are formed annularly around the chest tube and expanded after insertion to form a gas seal between the tube and the chest wall. The seal may be a bladder expanded by filling with a fluid or a wire mesh receptacle which is mechanically expanded and can also serve as the electrode.

20 Claims, 5 Drawing Sheets

INTRATHORACIC MECHANICAL, ELECTRICAL AND TEMPERATURE ADJUNCT TO CARDIOPULMONARY CEREBRAL RESUSCITATION, SHOCK, HEAD INJURY, HYPOTHERMIA AND HYPERTHERMIA

TECHNICAL FIELD

This invention relates generally to the field of methods and apparatus for treating cardiac arrest patients, patients in various forms of shock, patients in respiratory failure, patients suffering hypothermia and hyperthermia, and patients with head injury. More specifically, this invention relates to devices for inserting into the patient's thoracic cavity to alter intrathoracic pressure, cardiac electrical activity, intracranial pressure, lung volumes, and core body temperatures and methods for inserting and positioning these devices for treating these patients.

BACKGROUND ART

Approximately one million people per year have cardiac arrests in the United States. Less than ten percent of these people are discharged from the hospital alive without neurologic damage. This percentage of people discharged would be increased if the treatment available after the onset of cardiac arrest was improved. Five areas in which the treatment could be improved include: 1) artificial circulation during cardiopulmonary resuscitation (CPR), 2) defibrillation countershock techniques, 3) cardiac pacing, 4) cardiac monitoring, and 5) induction and maintenance of hypothermia.

The blood of a cardiac arrest patient is artificially circulated during CPR by cyclically compressing the chest. One major theory describing how artificial circulation is generated during CPR states that compression of the chest causes global increases in intrathoracic pressure. This increase in intrathoracic pressure in the thoracic compartment is evenly distributed throughout the lungs, the four chambers of the heart, as well as the great vessels in the chest. This increase in thoracic pressure becomes greater than in the compartments above and below the chest. These compartments mainly include the neck and head above the chest and the abdominal compartment below the diaphragm and chest. When thoracic pressure is increased above the pressures in these compartments, blood within the thoracic cavity moves to the head and abdomen with greater blood flow going towards the head. When the chest is released, the pressure within the thoracic cavity drops and becomes less than pressure within the head and abdomen, therefore, allowing blood to return to the thoracic cavity from the head and abdominal compartments. This theory of CPR-produced blood flow is termed the thoracic pump mechanism, whereby the entire thorax itself acts as a pump with the heart itself acting as a passive conduit for blood flow. This theory is different from the cardiac pump theory which states that compression of the chest produces blood flow by compressing the heart between the sternum and anterior structures of the vertebral column. In most patients, blood flow produced during chest compressions is likely a combination of the two theories. In each individual patient, blood flow during CPR depends on various factors such as body habitus, with thinner individuals relying more on the cardiac pump mechanism of blood flow and larger individuals with increased anterior-posterior chest dimension relying on the thoracic pump mechanism. Both mechanisms of blood flow have been shown to be present in animal and human studies. Regardless of which mechanism is invoked, currently performed standard chest compressions as recommended by the American Heart Association produces 30% or less of the normal cardiac output. This results in extremely poor regional cerebral and myocardial blood flow during CPR. This level of blood flow is usually insufficient to restart the heart and prevent neurologic damage. The purpose of CPR is to attempt to sustain the viability of the heart and brain until more definitive measures such as electrical countershock and/or pharmaco-therapy is administered to the patient.

Several techniques have been developed to take advantage of the thoracic pump mechanism of CPR-produced blood flow. One of these is the technique of simultaneous ventilation compression CPR (SVC-CPR). This technique involves inflating the lungs simultaneously during the chest compression phase of CPR. This causes larger increases in intrathoracic pressure than external chest compression alone without ventilation or ventilation alone without external chest compression. This has been shown in animal studies to result in higher cerebral blood flows than conventionally performed CPR. However, one major drawback is that coronary perfusion pressures are not uniformly increased and in some instances can be detrimentally decreased. Coronary perfusion pressure (CPP) is defined as the mean diastolic aortic pressure minus the mean diastolic right atrial pressure, and is the driving force of myocardial blood flow during CPR. When SVC-CPR was tested in a clinical trial no increase in survival was noted over standard CPR.

Another technique developed to take advantage of the thoracic pump mechanism of CPR is termed vest-CPR. This technique utilizes a bladder-containing vest analogous to a large blood pressure cuff and is driven by a pneumatic system. It is illustrated in U.S. Pat. No. 4,928,674. The vest is placed around the thorax of the patient. This pneumatic system forces compressed air into and out of the vest. When the vest is inflated, a relatively uniform decrease in the circumferential dimensions of the thorax is produced which creates an increase in intrathoracic pressure. Clinically this vest apparatus is cyclically inflated 60 times per minute with 100–250 mm of mercury pressure which is maintained for 40–50% of each cycle, with the other portion of the cycle deflating the vest to 10 mm of mercury. Positive pressure ventilation is performed independent of the apparatus after every fifth cycle. When studied clinically in humans and compared with manually performed standard external CPR, the vest apparatus produces significantly higher coronary perfusion pressure and significantly higher mean aortic, peak aortic and mean diastolic aortic pressures. However, these changes are not uniformly seen in all patients. Of note, when the vest has been studied in the laboratory and clinical settings, larger doses of epinephrine have been used to achieve these higher coronary perfusion pressures since the thoracic pump model would predict aortic, diastolic and right atrial diastolic pressures to be equivalent during the relaxation phase (when coronary perfusion occurs). No active deflation of the vest takes place, rather it is allowed to passively deflate. When this device is used, countershocks are performed by externally placed, self-adhesive defibrillator/pacer/monitor pads which are placed between the vest and skin of the patient.

Another new technique which takes some advantage of both the thoracic and cardiac pump mechanism of blood flow is called active compression-decompression CPR (ACDC-CPR). This technique utilizes a plunger-type device that is placed on the patient's sternum during cardiac arrest. The person performing chest compressions presses on this device which causes downward excursion of the anterior chest wall. What is unique is that the person then pulls up on the device. Since the device is attached to the sternum by suction, this causes the anterior chest to be actively recoiled instead of undergoing the usual passive recoil of standard external CPR. This active recoil is capable in many individuals of causing a decrease in intrathoracic pressure which is transmitted to the right atrium, thus lowering right atrial pressure during artificial diastole and in turn increasing coronary perfusion pressure. This negative pressure also has the effect of increasing venous return to the thoracic cavity which may enhance cardiac output. This negative pressure also may cause movement of air into the lung which may create some artificial ventilation. Factors such as body habitus and chest compliance which impact on the efficacy of ACDC-CPR have not been studied but are likely to have an effect. Persons with larger body habitus would receive less benefit from the technique.

In addition to artificial circulation, many patients also require a defibrillation countershock during CPR in order to re-start their heart. Defibrillation countershock therapy involves placing two electrodes near the heart and inducing a flow of electrical current through the chest and heart, and preferably through the left ventricle of the heart, which is the largest portion of the heart muscle that is fibrillating. The electrodes used have conventionally been hand-held paddles or adhesive pads, either of which are placed at different positions on the external surface of the patient's chest, sides and/or back. A defibrillation countershock with this electrode placement methodology is commonly called an external defibrillation countershock.

A sufficient electrical current density must be induced in the myocardium in order to defibrillate a fibrillating heart. Current density is defined as the amount of current per cross-sectional area of tissue. In addition, this required minimum current density must depolarize a certain minimum critical mass of the left ventricle of the heart in order to achieve defibrillation. For any given total current induced in the chest during a defibrillation countershock, the current density in the myocardium is generally inversely proportional to the distance between the countershock electrodes. This distance will vary depending on the location of the electrodes and the size of the patient's chest. If the electrodes are widely separated, more of the total current will pass through non-myocardial tissue. It is, therefore, advantageous to position the electrodes as close to the heart as possible in order to achieve defibrillation.

The machine used to deliver a defibrillation countershock as well as monitor and, when necessary, pace a patient's heart, is commonly called a defibrillator/pacer/monitor. All defibrillators today are clinically described as energy defibrillators in that the person administering countershock therapy presets the amount of electrical energy to be delivered to the patient during the countershock. For any preset energy level and electrode distance, the total current and current density induced in the myocardium is generally inversely proportional to the electrical impedance of the tissue lying between the electrodes. Although the myocardium has a relatively low impedance to electrical flow, tissue such as bone has a high impedance. For instance, structures such as the sternum, ribs and vertebral column have relatively high impedances to current flow. Some or all of these tissues, including skin, fat and cartilage, interpose the electrodes during the external countershock. It is, therefore, advantageous to position the electrodes so that there is the least possible amount of non-myocardial high impedance tissue between them.

It is further advantageous to use the smallest amount of current necessary to defibrillate the heart of the patient in cardiac arrest. Excessive current may cause irreversible structural damage to the myocardial tissue.

Conventional, internal countershock therapy utilizes the most ideal electrode placement and offers the highest probability of achieving defibrillation. In this method, the pair of electrodes is placed on opposite sides of and touching the left ventricle of the exposed heart, and the current is induced between the two electrodes. Under this circumstance, the distance between the electrodes is minimized and virtually no other tissues other than the myocardium interpose the electrodes. Virtually all the current flows through the left ventricle of the heart. This electrode placement requires the chest be open in order to expose the heart. Therefore, it is typically only performed under sterile conditions in an operating room. The procedures are impractical in an emergency setting outside the operating room.

There are several newly proposed methods of electrode placement meant to reduce the amount of high impedance tissue between the electrodes as well as reduce the distance between the electrodes. These involve placing one or more electrodes in the esophagus, stomach, esophagus and external chest, esophagus and stomach (patent pending) and esophagus, stomach, and external chest (patent pending). Examples of some of these are shown in U.S. Pat. Nos. 4,198,963 and 5,197,491 and PCT Application WO 92/06681. None of these proposed electrode orientations are directly in contact with the visceral or parietal surfaces of the thoracic cavity, lung or heart.

Patients suffer respiratory failure for numerous reasons. Normal respiration controlled by the brain is achieved by contraction and relaxation of respiratory muscles such as the diaphragm and intercostal muscles. The contraction of these muscles helps to produce negative intrathoracic pressures which draws air into the lungs. Relaxation of these muscles produces passive recoil of the chest and exhalation. During cardiac arrest when brain blood flow is insufficient, neural control of the respiratory muscles is lost. In states of trauma and other diseases, chest and lung compliance decreases which can cause fatigue of the respiratory muscles. When respiratory failure occurs, artificial ventilation is usually required by the technique of positive pressure ventilation. This usually requires endotracheal intubation. Positive pressure ventilation does not use negative pressure. Artificial means of ventilation by altering intrathoracic pressures by producing negative intrathoracic pressures might be advantageous and may reduce the need for endotracheal intubation. During standard external CPR and ACDC-CPR, it has been shown that if chest excursion is large enough, positive pressure ventilation may not be required for some time period.

One of the few resuscitative interventions found to improve neurologic outcome from cardiac arrest is induction and maintenance of cerebral hypothermia in the post resuscitation period. Although shown to be very effective, it is extremely difficult to rapidly produce a state of resuscitative hypothermia within a time frame immediately after restoration of spontaneous circulation following cardiac arrest. Although a decrease in cerebral temperature from 37° to 34° C. has proven to be neuro-protective, even this small drop of 3 degrees is difficult to produce rapidly. In order to be effective this mild degree of hypothermia must be produced within minutes of the resuscitation. Methods such as isolated head cooling by placement of the head in an ice bath or by nasopharyngeal cooling, injection of the carotid circulation with cooled solution, thoracic and peritoneal lavage, placement of the head and thorax in a cooling helmet and jacket, are all problematic in that hypothermia is not attained rapidly enough, or if attained cannot be maintained for a sufficient duration of time to be neuro-protective. Although cardiopulmonary bypass can produce a state of therapeutic hypothermia very rapidly, its institution either with traditional placement through a median sternotomy or through peripheral placement percutaneously via the femoral artery and femoral vein, is too time-consuming for it to be of practical use in the emergency setting. Thoracic and peritoneal lavage, although effective, are also somewhat time-consuming and cumbersome in the emergency setting especially when ongoing resuscitative efforts are required. Carotid flush is effective but would involve needle or catheter placement in the internal carotid artery which may be impractical, difficult to achieve, or unsafe. Although almost immediate brain cooling can be achieved with carotid flushing, once restoration of spontaneous circulation is achieved, continuous infusion would be required to maintain cerebral hypothermia. Cooling jackets and cooling helmets along with placement of the head in an ice bath require too long of a time period to be effective in rapidly reducing the cerebral temperature. The main problem with these techniques is that if cooling is not simultaneously accompanied by sufficient cerebral blood flow, rapid temperature drops are unlikely to occur. This is especially true of external cooling because the amount of blood flow and temperature gradient that would be required to cause rapid drops in core temperature is quite large. The same problems exist when attempting to rapidly induce hypothermia in victims of head trauma.

Therapeutic measures which have been shown to aid victims of head trauma include induction of therapeutic hypothermia and reductions in intracranial pressure. Hypothermia has been shown to improve the survival and reduce the amount of injured neurologic tissue. Several proposed mechanisms by which this happens are decreases in the metabolic requirements of the injured tissue, as well as decreases in the secretion of damaging neurotransmitters by the injured tissue. Currently the main mechanisms for reducing intracranial pressure involve the administration of diuretics such as furosemide and mannitol, administration of steroids which reduce swelling, removal of cerebral spinal fluid, elevation of the head which promotes venous drainage, administration of barbiturates which reduce the metabolic demand of brain tissue, hyperventilation producing hypocapnia and reduced cerebral blood flow which decrease intracranial pressure, and as a last resort, removal of less necessary parts of the brain itself. Production of hypothermia in head-injured patients has been limited to cooling blankets which produce whole body cooling. Although sometimes effective, whole body cooling is difficult to initiate early.

Prolonged exposure to cold or hot environments under certain conditions can result in life-threatening states of hypo- or hyperthermia, respectively. Patients may present in various forms of shock and/or various forms of altered mental status. In cases of hypothermia, an attempt is made to normalize the core body temperature as rapidly as possible. Methods have included passive rewarming with blankets and heating lamps, cardiopulmonary bypass, infusion of warmed intravenous fluids, peritoneal, bladder, gastric, thoracic, and mediastinal lavage, and breathing of warmed humidified air. Many of these methods are ineffective and are capable of only raising core temperature at a rate of 1° C. an hour. Some will be rendered totally ineffective based on the victim's circulatory status. Others such as peritoneal and thoracic lavage with warmed fluids are effective but time-consuming and difficult to control. In addition, they cannot help support the circulation during shock. Cardiopulmonary bypass is effective but is time-consuming and requires an extensive level of expertise.

Treatment of hyperthermic emergencies requires the ability to rapidly lower the body's core temperature to normal to avoid shock, cardiac arrest, and various forms of neurologic damage. Methods currently used are moderately effective and include ice packing, lavage of various body cavities with cooled fluids, and convection with water spray and fanning. Some of the methods will be totally ineffective based on the status of the patient's circulation. In addition, if countershock or pacing is required, safety hazards are present if the surface of the body is wet from the cooling technique used. In addition, none of the above methods will be capable of simultaneously supporting the circulation.

BRIEF DISCLOSURE OF INVENTION

The method of the invention is for treating a patient suffering from cardiac arrest, shock, respiratory failure, hypothermia, hyperthermia, or head injury. The method comprises alternately inflating and deflating a patient's thoracic cavity with a gas. Preferably this is performed by inserting one chest tube percutaneously in a patient's left hemithorax and inserting a second tube percutaneously in the patient's right hemithorax. A gas is then alternately pumped into and pumped out of the hemithoraces through the tubes. The gas may be heated or cooled before inflating the thoracic cavity with the gas in order to warm or cool the contents of the thoracic cavity, including the blood. The apparatus of the invention includes a tube for insertion through a hole in the chest wall into a hemithorax, a seal extending annularly around the tube to form a gas seal at the chest wall hole and a gas source, including a valve, connected to the tube to periodically supply gas under pressure through the tube into the hemithorax. Combined with these components are any one or more, and preferably all, of: (1) an exhaust pump, including a valve, connected to the tube and adapted to periodically deflate the hemithorax alternately with the inflating step; (2) a gas regulator, including a heat exchanger connected between the gas source and the tube for changing the temperature of gas supplied into the thorax; and (3) an electrode mounted to the tube and connected through a wire for connection to electronic medical equipment, such as a defibrillator/pacer/monitor.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other elements where such connection is recognized as being equivalent by those skilled in the art.

DETAILED DESCRIPTION

This invention is an improved apparatus for treating cardiac arrest patients, patients with arrhythmias, patients undergoing cardioversion, patients in various forms of shock, patients with need for monitoring and cardiac pacing, patients with respiratory failure, patients with head injury, and patients suffering hypothermia or hyperthermia. This invention comprises an improved method of creating artificial circulation to the heart and brain during cardiac arrest and other forms of shock while simultaneously rapidly producing states of therapeutic hypothermia. In addition, the method provides for a means to internally countershock, pace, and monitor the heart. The improved method comprises inserting a percutaneously placed, modified chest tube in both the right and left hemithorax of the patient. These tubes are placed using the Seldinger technique. There are several special properties of this percutaneous chest tube. These include multiple holes or special screens in the portion of the tube within the patient's thoracic cavity which allow rapid passage of gas in and out of the patient's thoracic cavity. In addition, there are two or more inflatable balloons or expandable screens which emanate from the chest tubes. These balloons or screens are conductive and, therefore, are capable of monitoring heart activity as well as passing current for countershocking and pacing. These balloons or screens also prevent dislodgement of the tubes from the thoracic cavity and prevent lung tissue from occluding the gas ports of the tube.

The improved apparatus further comprises an electrically driven pressure and vacuum pump with various pressure regulators, vacuum regulators, and solenoids. This creates the capability to actively introduce gas into the thoracic cavity, thereby producing positive intrathoracic pressure, as well as actively removing gas from the thoracic cavity, thereby producing active negative intrathoracic pressures in a timed fashion. These actions may also be timed and synchronized in various forms with the heart and respiratory rate. The gas introduced and removed from the thoracic cavity can also be temperature-controlled thus helping to regulate temperature as required in a particular setting. A thoracic binder is also placed about the chest when the device is used to produce artificial blood flow or support circulation in cardiac arrest or other forms of shock. This binder prevents outward chest excursion, thus enhancing the increase in intrathoracic pressure when gas is introduced into the thoracic cavity. The binder can be a band of adhesive tape wrapped onto itself around the chest. Alternatively, it may be a pant's belt or a flexible nylon strap with appropriate fasteners, such as Velcro.

There are many advantages of this device over other methods and techniques such as the vest-CPR apparatus. This device is electrically driven and requires no source of compressed air, therefore, making it portable. Although slightly invasive, paramedics are currently trained to place small catheters in the chest to decompress tension pneumothoraces. The fact that intrathoracic pressure is directly increased by pressurizing the internal thoraces means that intrathoracic pressure can be increased to a much greater degree than with the total external system of the vest-CPR apparatus. Therefore, rises in intrathoracic pressure are not limited by patient size or chest compliance.

By directly causing negative intrathoracic pressures, this device creates significant movement of air into and out of the lungs for providing ventilation, and thus avoiding the need for endotracheal intubation.

This device is also unique in that it can actively produce negative intrathoracic pressures by actively removing the previously introduced gas from the thoracic cavity with a vacuum mechanism. This drop in intrathoracic pressure to a negative degree has several advantages such as increasing venous return and therefore increasing cardiac output, decreasing right atrial pressure, thus increasing coronary perfusion pressure and increasing venous return from the head and therefore decreasing intracranial pressure. The device is also unique in that the hemithoraces can be synchronously or alternately inflated and actively deflated. This may offer some advantages in favorably increasing coronary perfusion pressure. These changes in negative intrathoracic pressure are much greater than that produced by ACDC-CPR and are not as dependent on patient size or thoracic compliance. ACDC-CPR also cannot be used to alternately change intrathoracic pressure between hemithoraces.

Another unique aspect of the device is its ability to introduce and remove gases of various temperature thus causing rapid changes in the patient's core temperature. This can be envisioned to be of extreme importance in resuscitating a victim of cardiac arrest or head injury where the previously discussed rapid induction of hypothermia may be therapeutic in decreasing the amount of brain injury. This may also be advantageous in rapidly decreasing cerebral temperature while simultaneously decreasing intracranial pressure in the victim of head trauma. The device's ability to rapidly alter temperature could also be envisioned to help victims of profound hypothermia or hyperthermia who are also in shock by normalizing temperature while supporting the circulation. Rapid changes of temperature are possible by exposing a large blood volume to a temperature gradient while producing better forward flow, thus making temperature-altered blood more available to the end-organ of interest.

GAS CIRCUIT

Figure 1:
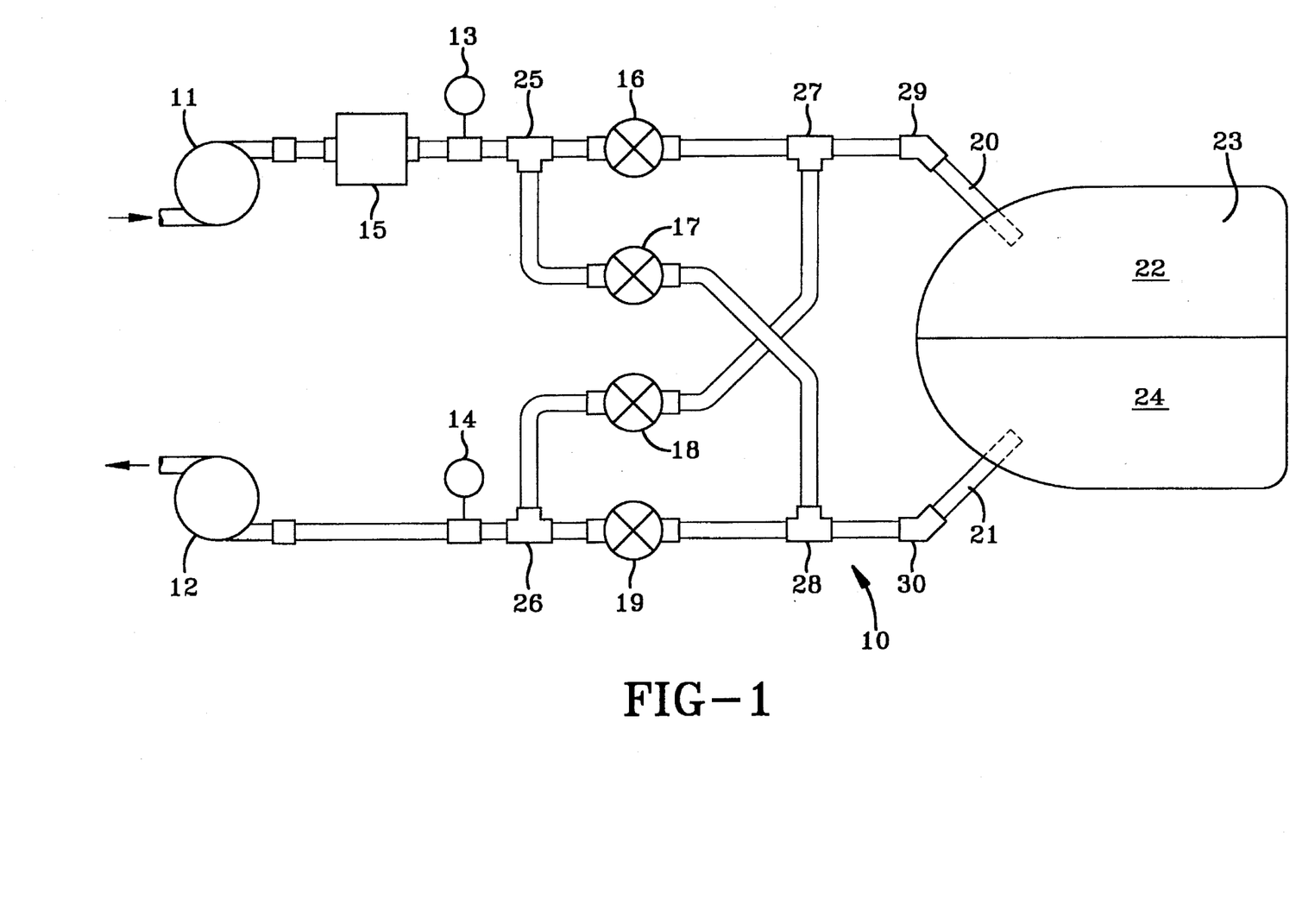
FIG. 1 is a schematic diagram of the gas circuit used to inflate and deflate the thoracic cavity in accordance with the present invention, as well as heat or cool the gas used for inflation and deflation.

Referring to FIG. 1, the preferred embodiment of the gas circuit 10 includes a pressure pump 11, vacuum pump 12, pressure regulator 13, vacuum regulator 14, gas temperature regulator 15, solenoid valve 16, solenoid valve 17, solenoid valve 18, solenoid valve 19, chest tube 20 and chest tube 21. Chest tube 20 and chest tube 21 are identical in their design, fabrication and function. They differ only in that chest tube 20 is associated with the right thoracic hemisphere 22 of the thoracic cavity 23 and chest tube 21 is associated with the left thoracic hemisphere 24 of the thoracic cavity 23. These elements of the gas circuit 10 are interconnected by gas tubing. The gas tubing has a preferred outside diameter of 1 cm and has sufficient wall thickness to withstand a gas pressure preferably in a range from −30 cm $H_2O$ to 150 cm $H_2O$ without collapsing or rupturing.

The operating inflation pressure for cardiopulmonary resuscitation should be somewhere in the pressure range from 100 cm $H_2O$ to 200 cm $H_2O$ to be effective and yet not cause damage to the patient. Currently we believe that 150 cm $H_2O$ is the preferred inflation pressure. The deflation pressure should be somewhere between −40 cm $H_2O$ and 0 cm $H_2O$ and preferably is in the range of −30 cm $H_2O$ to −20 cm $H_2O$. For other uses, such as cooling and head trauma, the pressure values can be considerably less. Inflation pressure can be in the range 0–50 cm $H_2O$ and deflation pumping can be considerably reduced between −20 cm $H_2O$ to 0 cm $H_2O$.

The pressure pump 11 and the vacuum pump 12 are powered either electrically or mechanically and are capable of producing a pressure and vacuum of 150 cm $H_2O$ and −30 cm $H_2O$, respectively, and a maximum gas flow rate of 180 L/min.

The gas temperature regulator 15 is electrically powered and is capable of regulating the gas temperature between −15° C. to 40° C. when gas flow through the gas temperature regulator 15 is 180 L/min. The gas temperature regulator 15 works in conjunction with the controller 55 shown in FIG. 7 and is generally composed of a separate electrically powered refrigerator unit and a separate electrically powered heater. Alternatively, the temperature regulator 15 may be composed of a device similar to a heat pump. In any event, the components of the temperature regulator are fabricated in such a way that incoming gas can be heated or cooled to a temperature set by the controls on the controller 55. The temperature regulator 15 also includes a thermocouple-type gas temperature sensor which is used as a feedback mechanism so that the controller 55 can control the power to the temperature regulator in order to regulate the gas temperature at the desired set value. The temperature regulator 15 may also include an insulated gas reservoir to store gas that has been cooled or heated by the refrigerator or heater prior to the gas entering the remainder of the gas circuit and thoracic cavity. A similar device is a servo controlled heater which is a part of a humidifier and heater used in a ventilator. Such a device is the subject of U.S. Pat. No. 4,110,419. The pressure regulator 13 and vacuum regulator 14 are mechanical regulators capable of regulating the pressure and vacuum in the circuit between 0 and 150 cm $H_2O$ and between 0 and −30 cm $H_2O$, respectively, in one cm $H_2O$ increments. Solenoid valves 16, 17, 18 and 19 are electrically powered and normally closed when they are de-energized. The gas circuit 10 includes t-connectors 25, 26, 27 and 28 as well as tube fittings 29 and 30 which are used in conjunction with the gas tubing to direct gas flow in the circuit in the preferred path of this invention.

CHEST TUBE

As indicated above, chest tube 20 and chest tube 21 are identical in design, fabrication and function and differ only by which thoracic hemisphere 22 or 24 of the thoracic cavity 23 they are inserted and associated. The following discussion, which refers to chest tube 20, applies equally and entirely to chest tube 21.

Figure 2:
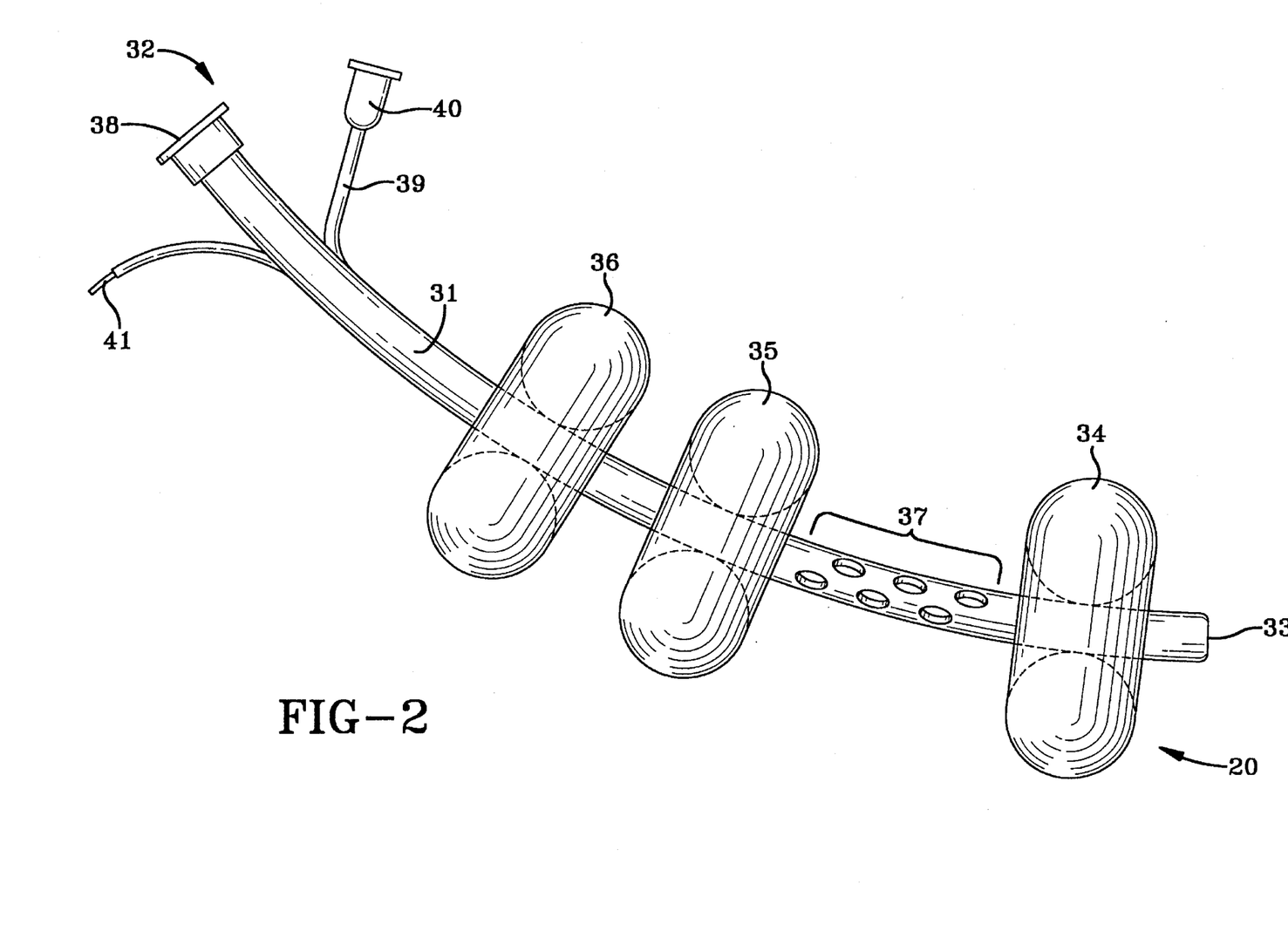
FIG. 2 shows one embodiment of the chest tube which is inserted through the chest wall and used, in conjunction with the gas circuit in FIG. 1 to inflate and deflate the thoracic cavity, alter core temperature and intracranial pressure as well as monitor, pace and countershock the heart.

Now, referring to FIG. 2, the chest tube 20 consists of a tube 31 having a preferred outside diameter of 1 cm and having sufficient wall thickness to withstand a gas pressure in a range from −30 cm $H_2O$ to 150 cm $H_2O$ without collapsing or rupturing and having a proximal end 32 and a distal end 33. A tube fitting 38 is adhered to the proximal end 32 of tube 31 which allows connection to the gas circuit 10 in FIG. 1 at the tube fitting 29. The distal end 33 of tube 31 is open-ended. Adhered circumferentially around tube 31 nearer its distal end 33 are three expansible, fluid-fillable, flexible-walled bladders; a distal bladder 34, located approximately 0.5 cm from the distal end 33 of tube 31, a medial bladder 35, located approximately 3 cm from the distal bladder 34, and a proximal bladder 36, located approximately 2 cm from the medial bladder 35. When these bladders are filled, as shown in FIG. 2, they each form roughly a donut shape with an outer diameter of approximately 5 cm. The tube 31 passes through what would be the hole in the three donut-shaped bladders and the long axis of tube 31 more or less passes through the axis and geometrical center of the three bladders. When these bladders are empty, it is intended that they fold around the exterior wall of tube 31 so that the maximum overall diameter of the chest tube 20 in the vicinity of the bladders is not greater than 1.05 times that of the diameter of tube 31 itself. It is intended that the distal bladder 34 is made of flexible, conductive material such as graphite-impregnated or silver-impregnated silicone so that the bladder, when filled with a fluid and in its operable position, will function as an electrode for both cardiac monitoring, cardiac pacing and countershock delivery.

A series of holes 37 which are bored through the wall of tube 31 and which communicate with the lumen of tube 31 from the exterior are evenly spaced longitudinally between distal bladder 34 and medial bladder 35 and evenly spaced circumferentially around the tube 31. It is intended that the distal bladder 34 and the medial bladder 35, when filled with a fluid, also function as spacers to prevent tissue from blocking the series of holes 37 when the distal end of the chest tube 20 is inside the chest and in its operable position and thus allows gas to flow into and out of the thoracic cavity through the operation of the gas circuit 10 in FIG. 1.

The lumen of the bladder filling tube 39 communicates with a lumen embedded in the side wall of tube 31 near the proximal end 32 of tube 31. A Luerlock fitting 40 is attached to the proximal end of bladder filling tube 39. The lumen embedded in the side wall of tube 31 extends from the proximal end 32 to near the distal end 33 of tube 31 and communicates with the interior of the proximal bladder 36, medial bladder 35 and distal bladder 34. With this arrangement, the bladders can be filled simultaneously with fluid from a syringe connected to the Luerlock fitting 40.

An electrode wire 41 covered with electrical insulation enters the side wall of tube 31 near its proximal end 32. The electrode wire remains embedded in the side wall and extends from the proximal end 32 to near the distal end 33 of tube 31 and connects electrically to the wall of distal bladder 34. With this arrangement, the electrode wire 41 forms the electrical connection between a defibrillator/pacer/monitor and the distal bladder 34 when the bladder functions as an electrode for cardiac monitoring, cardiac pacing and countershock delivery.

The intended operating position of chest tube 20 is with the chest wall interposed between the proximal bladder 36 and the medial bladder 35 with the proximal bladder 36 outside and the medial bladder 35 inside the thoracic cavity. Chest tube 20 is inserted using the Seldinger technique through a hole in the chest wall when all bladders are unfilled and folded around tube 31. The tube is advanced so that the chest wall lies between the proximal bladder 36 and the medial bladder 35. Then a fluid-filled syringe is attached to Luerlock fitting 40 and fluid is injected into the bladders thereby filling them. When the proximal bladder 36 and the medial bladder 35 are filled with a fluid, they form a securing mechanism so that the chest tube 20 will not move axially and they also form a virtual gas-tight seal between the chest tube 20 and the chest wall itself.

Figure 3:
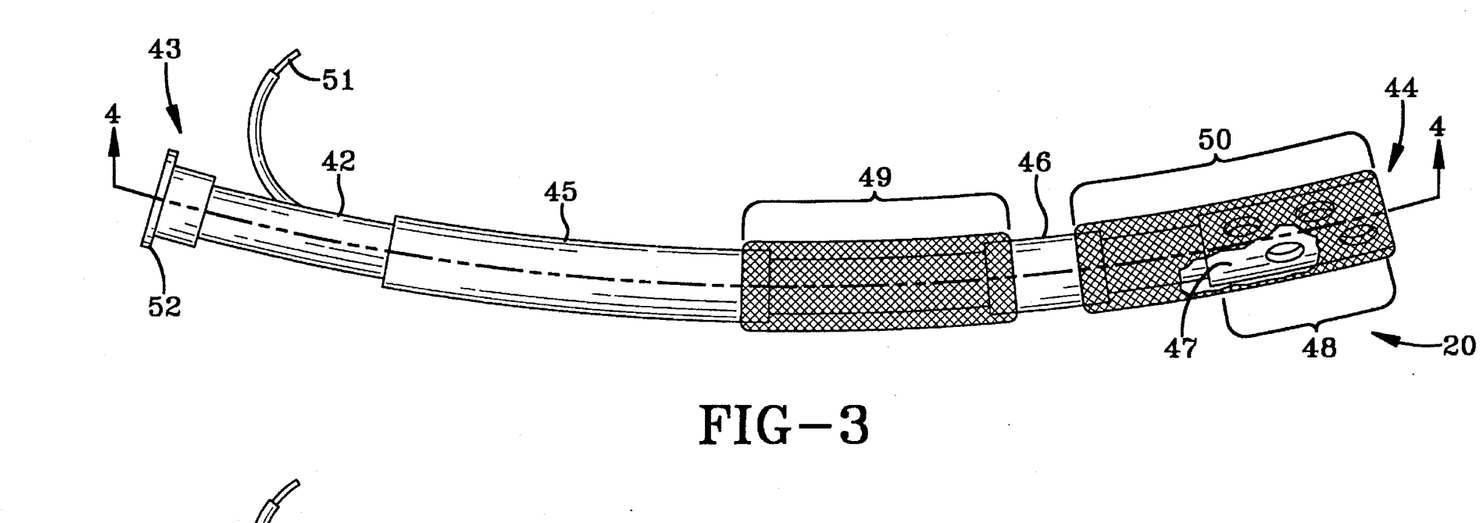
FIG. 3 is an alternative embodiment of the chest tube shown in its collapsed state ready for insertion through the chest wall.
Figure 4:
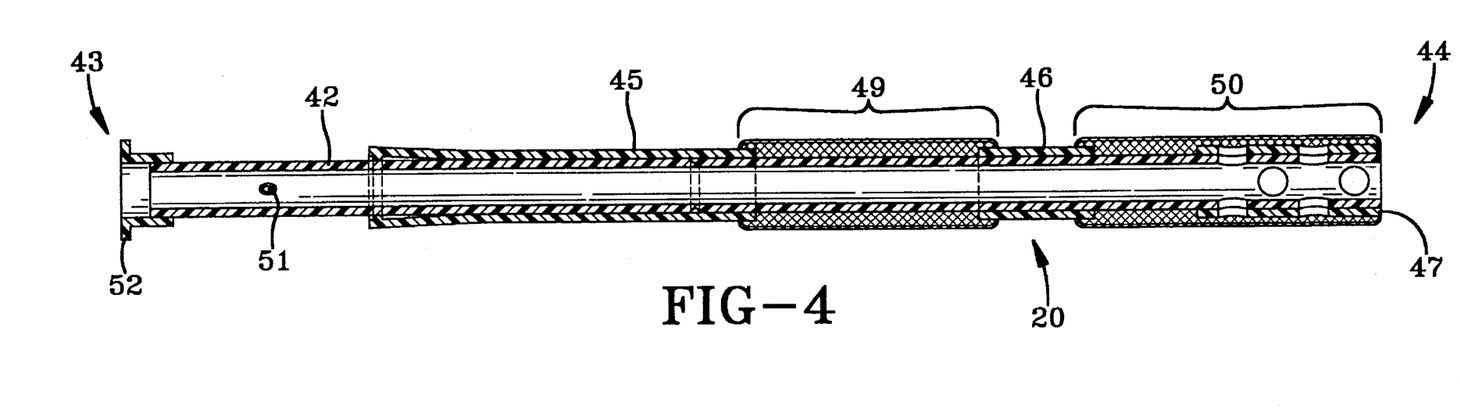
FIG. 4 is a cross-sectional view of the chest tube depicted in FIG. 3.

Referring to FIG. 3 and FIG. 4, an alternative embodiment of chest tube 20 consists of a tube 42 having a similar size and characteristics of tube 31 in FIG. 2. Tube 42 has a proximal end 43 and a distal end 44. A tube fitting 52 is attached to the proximal end 43 of tube 42 which allows connection to the gas circuit shown in FIG. 1 at the tube fitting 29. The distal end 44 of tube 42 is open-ended. Tube 45, tube 46 and tube 47 are telescoped over tube 42. Tube 45 and tube 46 have an inside diameter that approximates the outside diameter of tube 42 such that these tubes will slide with some resistance over the outside surface of tube 42. Tube 47 has an inside diameter similar to tubes 45 and 46. Tube 47 is adhered to the distal end 44 of tube 42. A series of holes 48 are bored through the wall of tube 42 and tube 47 which communicate with the lumen of tube 42 from the exterior. The series of holes 48 are evenly spaced circumferentially and longitudinally around tube 47 and that portion of tube 42 covered by tube 47. These holes, in conjunction with the open end of tube 42, allow gas to flow into and out of the thoracic cavity through the operation of the gas circuit 10 in FIG. 1.

Wire mesh 49 and wire mesh 50 are both similar in construction to a Chinese finger trap. They are both fabricated from wire fibers. Each wire fiber in the wire mesh extends from one end of the wire mesh to the other end and follows a path which encircles tube 42 forming a helix around tube 42. Adjacent wire fibers alternate in the direction they encircle tube 42. The wire fibers encircling tube 42 in one direction are woven or intertwined with the wire fibers which encircle tube 42 in the other direction. Depending on the construction of the wire mesh, each wire fiber may encircle tube 42 several times. Wire mesh 49 and 50 completely surround tube 42 at the indicated positions shown in FIG. 3 and FIG. 4. The fibers of wire mesh 49 and 50 are made of a conductive metal which has some degree of springiness such as spring steel. The proximal end of wire mesh 49 is attached to the distal end of tube 45 and the distal end of wire mesh 49 is attached to the proximal end of tube 46. In a similar manner, the proximal end of wire mesh 50 is attached to the distal end of tube 46 and the distal end of wire mesh 50 is attached to the distal end of tube 47 and tube 42. In the state shown in FIGS. 3 and 4, the maximum overall diameter of the chest tube 20 in the vicinity of each wire mesh is not greater than 1.05 times that of the diameter of tube 42 itself.

Wire mesh 50 functions as an electrode. An electrode wire 51 covered with electrical insulation enters the side wall of tube 42 near its proximal end 43. The wire 51 remains embedded in the side wall and extends from the proximal end 43 of tube 42 to the distal end 44 of tube 42 and connects electrically to the wire mesh 50. With this arrangement, the electrode wire 51 forms the electrical connection between the defibrillator/pacer/monitor and the wire mesh when wire mesh 50 functions as an electrode for cardiac monitoring, cardiac pacing and countershock delivery.

Figure 5:
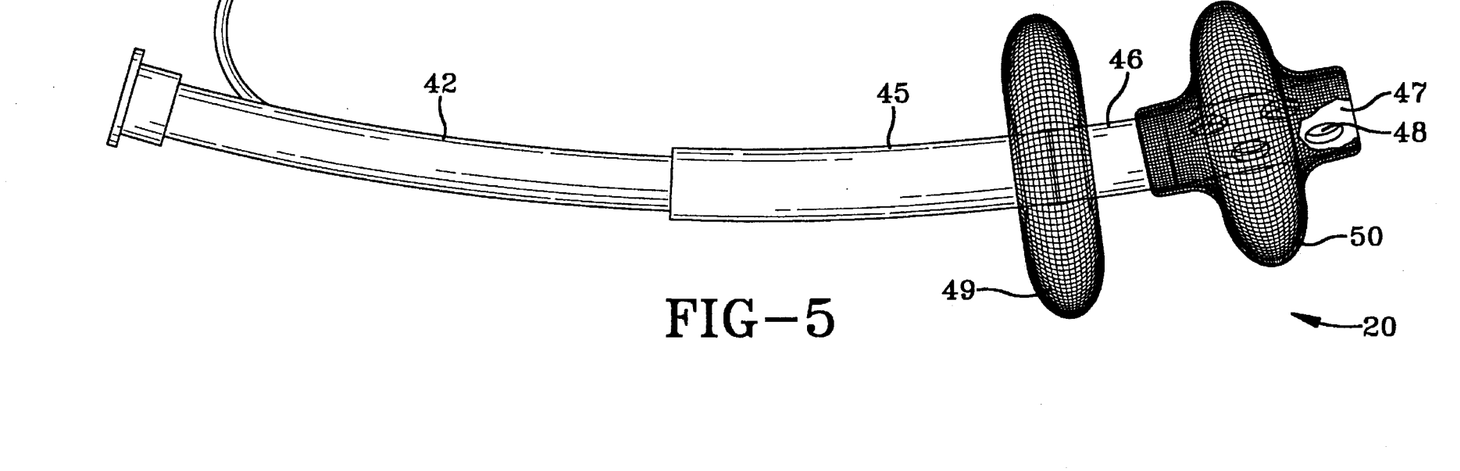
FIG. 5 shows the chest tube in FIG. 3 in its operable state.
Figure 6:
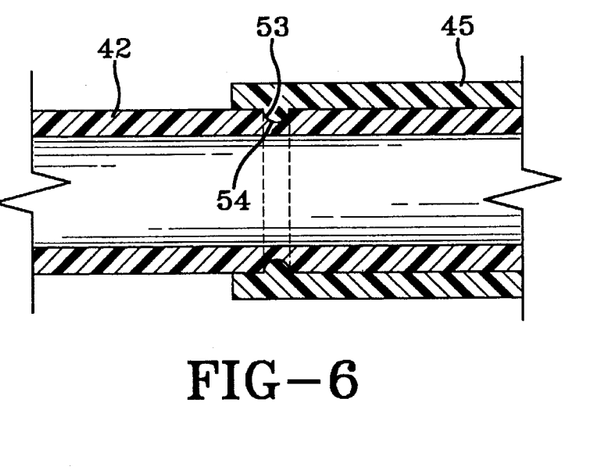
FIG. 6 is a detailed view of the locking mechanism of the chest tube depicted in FIG. 3.

Chest tube 20 is inserted, using the Seldinger technique, through a hole in the chest when chest tube 20 is in the state shown in FIG. 3. Chest tube 20 is advanced until the chest wall rests over tube 46. Then, holding tube 42, tube 45 is pushed distally, which consequently pushes tube 46 distally. This action compresses wire mesh 49 and 50 which causes them to expand and bulge out in their middle as shown in FIG. 5. Referring to FIG. 6, once the distal end of tube 45 contacts the proximal end of tube 46 and the distal end of tube 46 contacts the proximal end of tube 47, then rib 53 formed circumferentially on the inside surface of the proximal end of tube 45 snaps into channel 54, formed circumferentially on the outside surface of tube 42. This action locks the entire mechanism in the state shown in FIG. 5. Wire mesh 49 and 50 form a virtual gas-tight seal at the chest wall.

CONTROLLER

Figure 7:
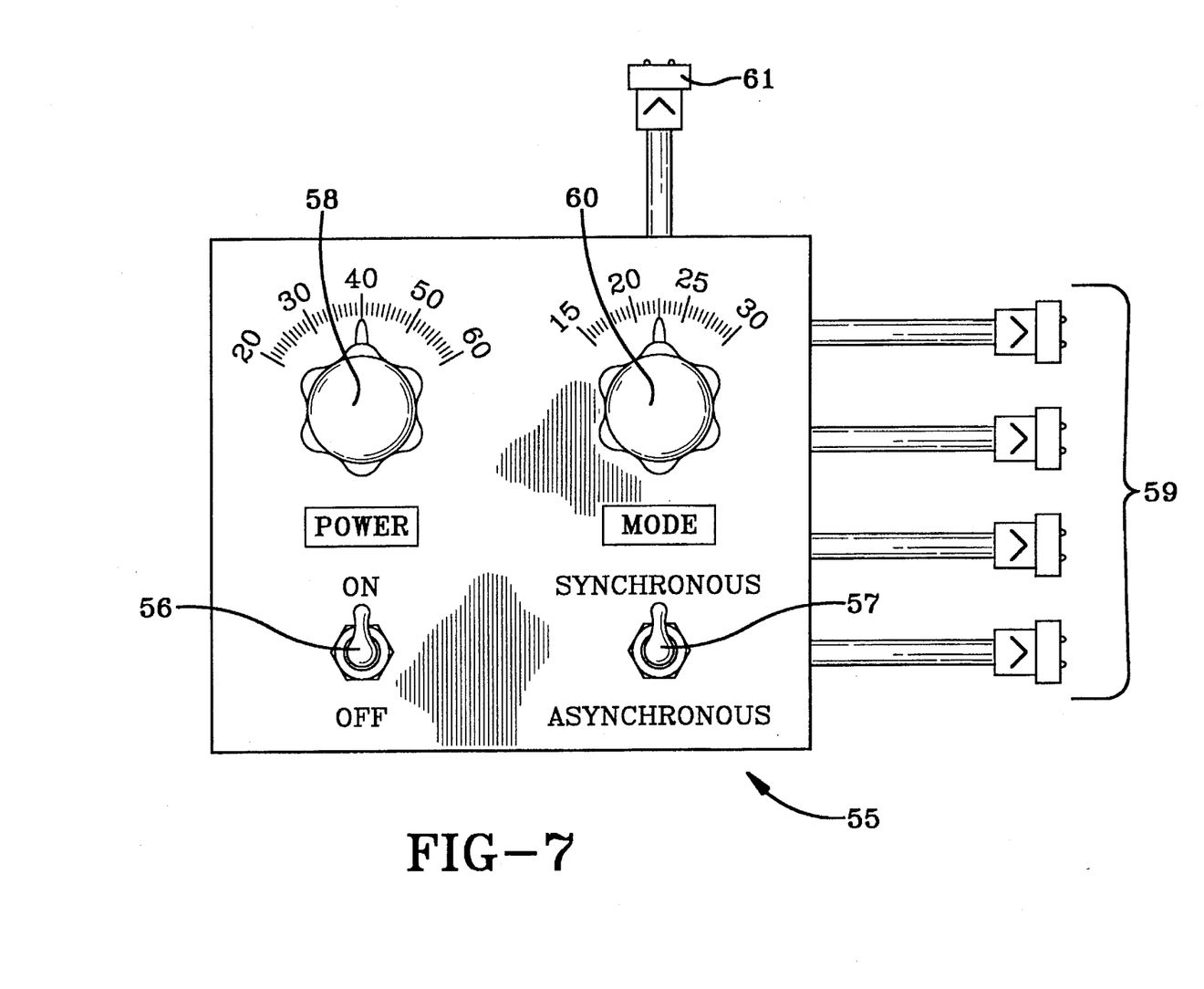
FIG. 7 shows the controller used to control the operation of the gas circuit depicted in FIG. 1.

Referring to FIG. 7, the controller 55 which controls the operation of the solenoid valves 16, 17, 18 and 19, as well as the temperature in the gas temperature regulator 15, contains the electric circuitry for controlling the electric power, mode of operation and cyclic rate of operation of gas circuit 10. Power switch 56 controls the main power to the controller 55 and thus controls the power to the solenoid valves and gas temperature regulator. Mode switch 57 controls the mode of operation of the gas circuit 10. The gas circuit 10 can operate in two distinct modes. In the synchronous mode of operation, the controller 55 alternately energizes solenoid valves 16 and 17 together and solenoid valves 18 and 19 together. In the asynchronous mode of operation, the controller 55 alternately energizes solenoid valves 16 and 19 together and solenoid valves 17 and 18 together. The rate controller 58 controls the rate at which the various solenoid valve combinations are energized and de-energized per minute. The rate controller 58 preferably controls the cyclic rate of the synchronous and asynchronous mode of operation from 20 cycles/min to 60 cycles/min in 1 cycle/min increments. The solenoid valve power cable set 59 consists of a set of 4 power cables, one power cable per solenoid valve. These power cables provide the electric power pathway for the controller 55 to energize the solenoid valves. Finally, temperature controller 60 controls the temperature of the gas temperature regulator 15 from 5° C. to 40° C. in 1° C. increments. Gas temperature regulator cable 61 delivers power and control signals from the controller 55 to the gas temperature regulator 15.

DESCRIPTION OF THE SYNCHRONOUS MODE OF OPERATION

Referring to FIGS. 1 and 7, with the mode switch 57 in the synchronous position, the power switch 56 in the on position, and, for example, the rate controller 58 set to 60 cycles/min, the controller 55 energizes solenoid valves 16 and 17 and de-energizes solenoid valves 18 and 19 in the first half of the cycle. Gas flows from the pressure pump 11, through the gas temperature regulator 15 at a pressure set by the pressure regulator 13. Gas flow is split at t-connector 25 and flows to solenoid 16 and solenoid 17. The gas flows from solenoid 16 through chest tube 20 and into the right thoracic hemisphere 22 of thoracic cavity 23. Gas cannot flow through solenoid valve 18 from t-connector 27 because it is de-energized during the first half of the cycle. Simultaneously, the gas flows from solenoid 17 through chest tube 21 and into the left thoracic hemisphere 24 of thoracic cavity 23. Gas cannot flow through solenoid valve 19 from t-connector 28 because it is de-energized during the first half of the cycle. During the first half of the cycle the volume of gas in the left and right thoracic hemispheres increases simultaneously thereby increasing the intrathoracic pressure which compresses the heart, thereby forcing blood out of the heart and into the systemic and pulmonary circulation.

In the second half of the cycle the controller 55 energizes solenoid valves 18 and 19 and de-energizes solenoid valves 16 and 17. A vacuum is created by the vacuum pump 12 at the vacuum set by the vacuum regulator 14. Therefore, gas flows from the left thoracic hemisphere 24 into chest tube 21 and through solenoid valve 19. Gas cannot pass through solenoid valve 17 because it is de-energized during the second half of the cycle. Simultaneously, gas flows from the right thoracic hemisphere 22 into chest tube 20 and through solenoid valve 18. Gas cannot pass through solenoid valve 16 because it is de-energized during the second half of the cycle. The gas from solenoid valves 18 and 19 combines at t-connector 26 and flows to the vacuum pump 12. During this half of the cycle the volume of gas in the left and right thoracic hemispheres decreases thereby decreasing the intrathoracic pressure which decompresses the heart, thus pulling blood into the heart from the systemic circulation.

DESCRIPTION OF THE ASYNCHRONOUS MODE OF OPERATION

Again referring to FIGS. 1 and 7, with the mode switch 57 in the asynchronous position and the power switch 56 in the on position, the controller 55 energizes solenoid valves 16 and 19 and de-energizes solenoid valves 17 and 18 in the first half of the cycle. Gas flows from the pressure pump 11, at a pressure set by the pressure regulator 13, through the gas temperature regulator 15, through solenoid valve 16, through chest tube 20 and into the right thoracic hemisphere 22 of thoracic cavity 23. Gas cannot flow through solenoid valve 17 from t-connector 25 because it is de-energized during the first half of the cycle. Similarly, gas cannot flow through solenoid valve 18 from t-connector 27 because it is de-energized during the first half of the cycle. A vacuum is created in the circuit by vacuum pump 12, at the vacuum set by vacuum regulator 14. Therefore, gas flows from the left thoracic hemisphere 24 into the chest tube 21 and through solenoid 19. Gas cannot flow from solenoid valve 17 through t-connector 28 because it is de-energized during the first half of the cycle. Similarly, gas cannot flow from solenoid 18 through t-connector 26 because it is de-energized during the first half of the cycle.

During the second half of the cycle, the controller 55 energizes solenoid valves 17 and 18 and de-energizes solenoid valves 16 and 19. Gas flows from the pressure pump 11, at a pressure set by the pressure regulator 13, through the gas temperature regulator 15, through solenoid valves 17, through chest tube 21 and into the left thoracic hemisphere 24 of thoracic cavity 23. Gas cannot flow through solenoid valve 16 from t-connector 25 because it is de-energized during the first half of the cycle. Similarly, gas cannot flow through solenoid valve 19 from t-connector 28 because it is de-energized during the first half of the cycle. A vacuum is created in the circuit by vacuum pump 12, at the vacuum set by vacuum regulator 14. Therefore, gas flows from the right thoracic hemisphere 22 into the chest tube 20 and through solenoid 18. Gas cannot flow from solenoid valve 16 through t-connector 28 because it is de-energized during the first half of the cycle. Similarly, gas cannot flow from solenoid 19 through t-connector 26 because it is de-energized during the first half of the cycle.

SUMMARY OF THE ADVANTAGES AND USES OF THE INVENTION

1. Cardiac arrest:
 a) Provide artificial circulation by producing positive and negative intrathoracic pressures.
 b) Intrathoracic pressures may be produced synchronously or asynchronously.
 c) Capable of intrathoracic cardiac ECG monitoring, pacing, and electrical countershock.
 d) Capable of providing ventilatory support through fluctuations in intrathoracic pressure.
 e) Capable of producing and maintaining therapeutic hypothermia by introducing cooled gases into the thoracic cavity.
 f) Capable of supporting post arrest circulation.
2. Other forms of shock:
 a) Provide circulatory and ventilatory support as above to varying degrees. Can be timed with heart rate and ventilatory rate.
 b) Can produce changes in core body temperature as needed.
3. Respiratory failure:
Provides ventilatory assistance by causing positive and negative fluctuations in intrathoracic pressure.
4. Head injury:
 a) Capable of decreasing intracranial pressure by causing larger and more sustainable decreases in intrathoracic pressure thus promoting venous return from the head.
 b) Capable of rapidly producing and maintaining state of therapeutic hypothermia by introducing cooled gas into the thoracic cavity.
5. Injury from hypothermia or hyperthermia:
 a) Capable of rapidly normalizing core body temperature by introducing warmed or cooled gases into the thoracic cavity.
 b) Capable of supporting the circulation as in 1 and 2 above.
 c) Capable of providing electrical support by intrathoracic pacing, countershock and monitoring as needed.

While certain preferred embodiments of the present invention have been disclosed in detail, it is to be understood that various modifications may be adopted without departing from the spirit of the invention or scope of the following claims.

We claim:

1. A method for treating a patient suffering from at least one of the conditions of cardiac arrest, shock, respiratory failure, hypothermia, hyperthermia, and head injury, the method comprising: alternately inflating and deflating a patient's thoracic cavity with a gas externally of the patient's lungs.

2. A method in accordance with claim 1 wherein said method more particularly comprises:
 (a) inserting a first tube percutaneously in a patient's left hemithorax, so the tube has an intrathoracic, distal end and an external, proximal end;
 (b) inserting a second tube percutaneously in a patient's right hemithorax so the tube has an intrathoracic, distal end and an external, proximal end; and
 (c) alternately pumping a gas into and pumping the gas out of the external end of said tubes.

3. A method in accordance with claim 2 more particularly comprising alternately (a) inflating both of a patient's left and right hemithoraces simultaneously and (b) deflating the hemithoraces simultaneously.

4. A method in accordance with claim 2 more particularly comprising alternately inflating a first one of a patient's hemithoraces while simultaneously deflating the patient's second hemithorax followed by inflating the patient's second hemithorax while deflating the first hemithorax.

5. A method in accordance with claim 1 and further comprising binding the chest to restrict outward chest excursion.

6. A method in accordance with claim 1 and further comprising changing the temperature of the gas before inflating the thoracic cavity with the gas.

7. A method in accordance with claim 1 wherein the deflating comprises pumping gas out of the thoracic cavity in alternation with the inflating.

8. A method in accordance with claim 7 wherein the alternate inflation and deflation is between a pressure exceeding 100 cm of $H_2O$ and a subatmospheric pressure.

9. A method in accordance with claim 8 wherein the pressures are substantially 150 cm of $H_2O$ and substantially in the range of $-30$ cm of $H_2O$ to $-20$ cm of $H_2O$.

10. A method in accordance with claim 8 and further comprising binding the chest to restrict outward chest excursion.

11. A method in accordance with claim 10 wherein said method more particularly comprises:

(a) inserting a first tube percutaneously in a patient's left hemithorax, so the tube has an intrathoracic, distal end and an external, proximal end;

(b) inserting a second tube percutaneously in a patient's right hemithorax so the tube has an intrathoracic, distal end and an external, proximal end; and (c) alternately pumping a gas into and pumping the gas out of the external end of said tubes.

12. A method in accordance with claim 11 more particularly comprising alternately (a) inflating both of a patient's left and right hemithoraces simultaneously and (b) deflating the hemithoraces simultaneously.

13. A method in accordance with claim 11 more particularly comprising alternately inflating a first one of a patient's hemithoraces while simultaneously deflating the patient's second hemithorax followed by inflating the patient's second hemithorax while deflating the first hemithorax.

14. A method in accordance with claim 11 and further comprising cooling the gas before inflating the thoracic cavity with the gas to induce mild to moderate cerebral hypothermia.

15. An apparatus for treating a patient suffering from at least one of the conditions of cardiac arrest, shock, respiratory failure, hypothermia, hyperthermia, and head injury, the apparatus comprising:

(a) a chest tube for insertion through a hole in a patient's chest wall into a first hemithorax and having a distal opening and a proximal opening in communication through the chest tube;

(b) a first collapsible and expandable seal extending annularly around the chest tube between the openings, the first seal being collapsible to a reduced diameter to facilitate insertion through said hole and being expandable after insertion and adapted to form a gas seal at said hole; and (c) a second collapsible and expandable gas seal extending annularly around the chest tube between the first seal and the distal opening and spaced from the first seal by a distance corresponding to chest thickness.

16. An apparatus in accordance with claim 15 wherein each of said seals comprises a different fluid inflatable, flexible bladder.

17. An apparatus in accordance with claim 16 wherein each of said seals comprises a different flexible wire mesh receptacle.

18. An apparatus in accordance with claim 17 wherein at least one wire mesh receptacle includes externally exposed metal for operating as an electrode and is connected to a wire leading to the proximal side of the seals for connection to electronic medical equipment.

19. An apparatus in accordance with claim 18 wherein each of the wire mesh receptacles is cylindrical in its collapsed state and surrounds the chest tube with one receptacle being more distal and the other being more proximal, the mesh receptacles having juxtaposed ends attached to an intermediate slide tube in telescoping arrangement around the chest tube, the more distal wire mesh receptacle having a distal-most end fixed to the chest tube near the distal end of the chest tube, and the more proximal receptacle having a proximal-most end attached to an external slide tube in telescoping relation about the chest tube.

20. An apparatus in accordance with claim 19 wherein the chest tube is provided with a plurality of holes in the tube sidewall radially inwardly of the more proximal wire mesh receptacle.

* * * * *

UNITED STATES PATENT AND TRADEMARK OFFICE
CERTIFICATE OF CORRECTION

PATENT NO. : 5,474,533
DATED : Dec. 12, 1995
INVENTOR(S) : Ward et al.

It is certified that error appears in the above-indentified patent and that said Letters Patent is hereby corrected as shown below:

Column 9, line 25, delete "-15°C." and insert therefore --5°C.--.

Signed and Sealed this

Fifth Day of March, 1996

BRUCE LEHMAN

Attest:

Attesting Officer

Commissioner of Patents and Trademarks